United States Patent [19]

Schreiber

[11] Patent Number: 5,190,455
[45] Date of Patent: Mar. 2, 1993

[54] ARTICULATOR APPARATUS

[76] Inventor: Hans Schreiber, Mierendorffstrasse 2, 6940 Weinheim, Fed. Rep. of Germany

[21] Appl. No.: 309,152

[22] Filed: Feb. 13, 1989

[30] Foreign Application Priority Data

May 18, 1988 [DE] Fed. Rep. of Germany ....... 3816820
May 26, 1988 [DE] Fed. Rep. of Germany ....... 3817867

[51] Int. Cl.$^5$ ............................................ A61C 11/00
[52] U.S. Cl. ........................................ 433/54; 433/55; 433/60; 433/63; 433/65
[58] Field of Search ................... 433/54, 55, 56, 60, 433/63, 65

[56] References Cited

U.S. PATENT DOCUMENTS

| | | | |
|---|---|---|---|
| 2,621,407 | 12/1952 | Schlesinger | 433/65 |
| 2,754,588 | 7/1956 | Cordell | 433/60 |
| 3,653,126 | 4/1972 | Hansen | 433/60 |
| 3,750,289 | 8/1973 | Guichet | 433/60 |
| 3,885,311 | 5/1975 | Lawler et al. | 433/65 |
| 4,624,639 | 11/1986 | Wong | 433/63 |
| 4,668,189 | 5/1987 | Levandoski | 433/55 |

Primary Examiner—John J. Wilson
Attorney, Agent, or Firm—Staas & Halsey

[57] ABSTRACT

A method and apparatus for performing a head-related model incorporating for transferring a jaw model between articulators of different types. The apparatus for the head-related incorporation of jaw models includes an articulator base plate, a ground plate connected to the articulator base plate and a cylinder having a cylindrical cavity connected vertically to an upper surface of the ground plate. A piston is inserted in the cylindrical cavity. A carrier plate is connected to the end of the piston opposite the articulator base plate. A split cast plate is positioned on the carrier plate and exactly repositionable via magnetic connection between the split cast plate and the carrier plate. A fixation element is connected to the carrier plate. An articulator mounting plate is supported by and connected to the split cast plate via a hardened viscous medium.

35 Claims, 17 Drawing Sheets

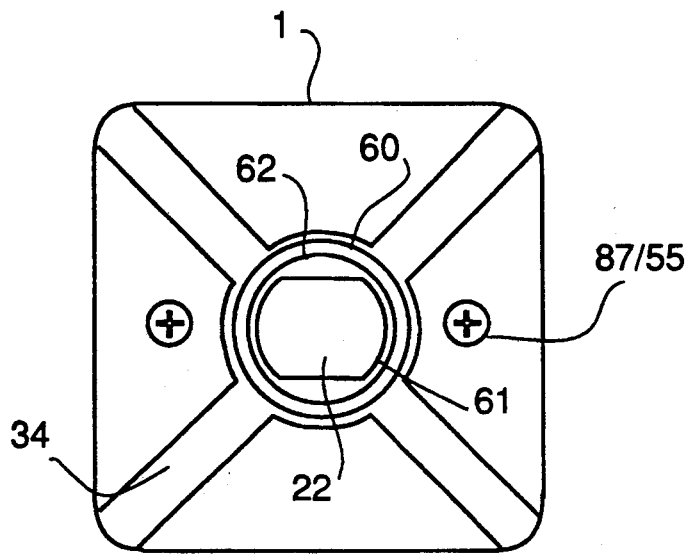
Fig. 20
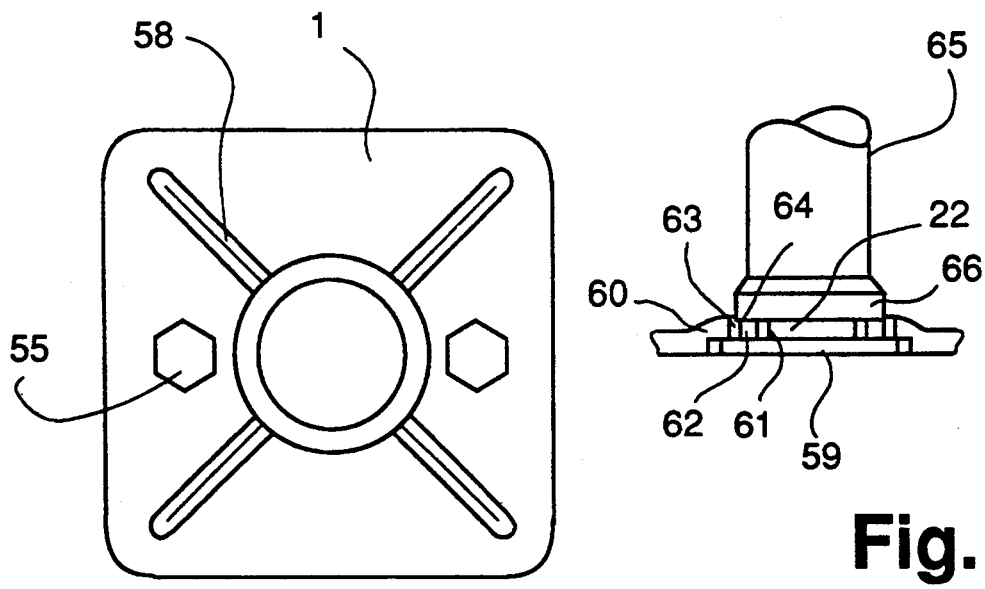
Fig. 21
Fig. 22

ARTICULATOR APPARATUS

BACKGROUND OF THE INVENTION

1. Field of the Invention

The present invention relates to a method and apparatus for identical head- and centric block related incorporation of jaw models into the most common articulator system.

2. Description of the Related Art

In the field or prosthetics, ground and bridge technique as well as in the frame work of functional diagnostics, after taking pressure forms from the patient, jaw models are prepared and incorporated or articulated into so-called articulators.

Thereby these apparatuses simulate the movement of the jaw of the patient, whereby in addition to the pure opening and closing movement of the lower jaw via a rotation axis by means of both jaw hinge heads, forward and sideward movements can also be simulated.

Naturally such a simulation can take place only more or less exactly, whereby the articulator type determines, which information content from the patient can be entered to simulate the jaw movement. The extent of this information entering decides also about which information content the apparatus can give back and/or by which information content prosthetic work prepared therein can be codetermined.

In the case of more demanding, partially adjustable articulators, in particular with fully adjustable apparatuses, the head-related upper jaw incorporation is obligatory. In other words, the upper jaw model in its special situation to the artificial jaw hinges of the articulator is incorporated in such a way as corresponds closely to the case of the patient. In practice, this is made possible by a so-called "face arc", which takes the position of the upper jaw in relation to the jaw hinges and to a deliberately determined plane, e.g., the hinged axis-orbital plane. In the case of some types of apparatuses it is possible to adjust to this plane further reference parameters such as hinge tour bending or the Bennett-angle.

The lower jaw model incorporation takes place via a so-called centric block registrate, whereby the patient preferably bites into a wax piece. Afterwards, with the help of the dentist or orthodontist, the lower jaw is laid into the so-called centric jaw hinge position or the terminal hinge axis position.

If a prosthetic work requires, for example, a bite lifting then this takes place in practical laboratory practice, in that after upper and lower jaw model incorporation the articulator is opened to the desired extent by hinge movement via its rotation axis.

It is natural that in the case of this procedure, mistakes necessarily occur, if the arrangement of the upper jaw model to the articulator rotation axis shows a relation other than the corresponding relation at the patient.

In the case of the utilized face arc types only few apparatuses are compatible with different articulator systems. This means that the dentist has commit himself in the case of a planned head-related model incorporation to an articulator type and thus has to commit the corresponding face arc. Accordingly, the laboratory which constructs the prosthetic piece is committed to this articulator type.

However, all common articulator systems function principally similarly, whereby gypsum carrier plates are premounted and connected with the models by means of a gypsum base.

Different articulators differ from each other in the building height, the arrangement of the artificial jaw hinges and in the dimensions of the gypsum carriers.

Articulators are comparable to computers since they, as described above, deliver information, if they are first fed with information.

In normal routine work, partially adjustable articulators suffice in which a few parameters, such as, for example, the hinge bending or the so-called Bennett-angle, are predetermined.

In the case of fully adjustable articulators, parameters can be individually entered besides other parameters. In the case of partially adjustable apparatuses, there already exists in many cases the possibility of a head-related upper jaw incorporation.

According to the design of the respective articulator upper jaw are consequently for the different articulator systems, a gypsum base of different height results. The building height of the articulator determines, after the arrangement of the lower jaw model to the built-in upper jaw model, the height of the lower jaw gypsum base.

The possibility to utilize two apparatuses simultaneously without new mounting, that is, the transferability of a premounted model from one apparatus to another, which can be of importance in work with an outside laboratory, is so far known only with the same type of articulator.

SUMMARY OF THE INVENTION

An object of the present invention thus is to provide a method and apparatus to carry out a head-related model incorporation, which has been carried out with face arc A in articulator A to transfer to a deliberate articulator B, with the respective face arc B, without having to the measurements for the bead model again.

With the present invention it is even possible to transfer head-relatedly built-in models from articulator A to an articulator C, for which a face arc has not at all been designed by the producer. Thus, the taking and the secure repositioning of jaw models is made possible, while the synchronization not only of identical articulator types but even of different articulator types and designs is made possible.

The application of the method of the invention and the corresponding apparatus is of advantage particularly in cases where articulators of the same or different design by utilization of a corresponding split cast plate were synchronized, so that models which can be lifted from that split cast plate by magnetic force and exactly be repositioned, can be transferred to other articulator types synchronized with the same split cast plate.

The particular advantage of the invention is accordingly seen in that the dentist utilizes his usual face arc and for control his articulator, whereby the laboratory after accepting the corresponding parameters may use a different articulator, which possibly is capable of fulfilling further-reaching single tasks.

The apparatus for the head-related incorporation of jaw models according to the present invention includes an articulator specific articulator base plate and a mobile fixable ground plate, upon which is vertically arranged a sleeve in which a piston is mobile in the vertical direction as well as axially rotatable and fixable arranged, at the upper end of which a carrier plate for the exact incorporation of a model carrier of split cast plate is fixed, whereby the position of the base plate and the vertical and axial position of the piston are chosen in such a way that an orientation arc fixed at the carrier plate via a transverse rod with preferentially separate and precisely guided side arms is adjusted in such a way that needle markings on the side arms can be aimed to the rotation axis of the articulator, whereby the split cast plate positioned on the carrier plate is then combined with an articulator mounting plate mounted at an articulator upper jaw arm via an intermediate medium such as e.g. gypsum, plastic or other, reversibly.

The special arrangement of the model plate to the articulator mounting plate in the area of the upper jaw takes place with the starting articulator with the minimal distance between articulator upper jaw arm and hinge axis preferably solidly flush, whereby the model or split cast plate of the carrier plate lies on the mounted apparatus.

A special arrangement of model plate and mounting plate with further articulator types is achieved in such a way that the position of the upper jaw model plate of the starting articulator is taken via the adjusted orientation arc, and after transposition of the apparatus into the to be synchronized articulator by means of adding the ground plate to the compatible articulator base plate, this determined relation to the hinge axis by vertical and horizontal (axial) movement of the apparatus upon incorporation of the identical model or split cast plates is taken into consideration in an analogous way by utilization of an articulator compatible mounting plate.

The arrangement of the lower jaw-split cast plates for the centric synchronization takes place via a centric-relation-block, whereby the apparatus with a minimal distance from articulator lower jaw arm to hinge axis serves as starting articulator and whereby this articulator was already adjusted in a hinge axis related manner. The special arrangement of the model plate to the mounting plate is, in the case of the starting articulator, principally arbitrary, optimally, however, horizontally and possibly flush. With the following articulator type the special arrangement of the respective lower jaw split cast plate to the hinge axis related built in upper jaw split cast plate with the centric-relation-block produced in the starting articulator is achieved.

An especially preferred embodiment is characterized in that the articulator base plate features threads and millings, which serve for the incorporation into the respective articulator type. These threads and millings may be present also as exchangeable inset parts, which thus assure a greater compatibility. Moreover, on the articulator base plate, additional thread borings are arranged which serve for the fixation of the base plate.

A further preferred embodiment is characterized in that the base plate is equipped with a long hole or slot which is preferably directed in direction of the articulator and thus allows the movability of the ground plate in the case of nonactivated screwing to the articulator base plate in an axial3 direction, which permits a rotation movement. Also, according to the strength of the fixation screw, a bodily side movement of the ground plate is permitted, whereby an activation of the fixation screw fixes the ground plate on the articulator base plate.

A further particularly preferred embodiment of the present invention is characterized in that the articulator base plate carries for the head-related incorporation of jaw models parallel to the articulator specific millings a positive or a negative relief, which corresponds with the negative or positive relief of the base plate in such a way that the base plate is only axially movable on the articulator base plate. A fixation screw provides for fixation of the base plate and interacts by a preferably symmetrically arranged long holes of the base plate laid into the articulator base plate.

A further especially preferred embodiment is characterized in that the base plate carries in preferably centric position a sleeve or a tube in a vertical position which accepts exactly guided a round rod or, because of savings of material, a further tube, which is movable in the vertical direction and axially rotatable and which can be fixed via a fixation screw.

A further especially preferred embodiment is characterized in that in preferably centric position of the base plate a round rod is vertically arranged, by means of which an exactly produced sleeve or a tube is vertically movable and axially rotatably movable and can be fixed via a fixation screw.

A further especially preferred embodiment is characterized in that the base plate carries instead of a round rod a vertically oriented differently formed profile in which a flush movable like second profile allows vertical movability and fixability.

A further especially preferred embodiment is characterized in that the base plate features several guidance elements like sleeves, round rods or profiles.

A further especially preferred embodiment is characterized in that for the head-related incorporation of jaw models at the flushly prepared inner rod or the inner sleeve, an exact vertical direction marking is arranged, which corresponds with the second marking at the outer sleeve and which enables to fix the turning direction or the position of the inner rod with the mounted carrier plate at a single arrangement of sleeve and rod.

A further special preferred embodiment is characterized in that on the vertically movable sleeves, round rods or profiles, a carrier plate is arranged which carries on the side opposed to the fixation a negative or positive relief which is suitable for the exact acceptance of a split cast plate which again with its relief can accept a jaw model exactly repositionable.

A further especially preferred embodiment is characterized in that in the carrier plate an iron core or a small iron plate is set for holding the split cast plate which carries as a cooperating counter part a magnet.

A further especially preferred embodiment is characterized in that in the carrier plate a magnet is sunk for holding the split cast plate which carries an iron core or a small iron plate.

A further especially preferred embodiment is characterized in that at a carrier plate a holding mechanism is arranged which accepts a jaw shaped orientation arc preferably of round material, and whereby this frame can be moved with its transverse arm in the holding mechanism as well as rotatably and also side-wise in such a manner that its parallel side arms can be directed symmetrically as compared to the rotation axis of the articulator.

A further especially preferred embodiment is characterized in that for the head-related incorporation of a jaw model, the orientation arc in its transverse arm is solidly fixed and the side arms via a hinge each are rotatably and fixably arranged.

A further especially preferred embodiment is characterized in that on the side arms of the orientation arc for more exact adjustment to the turning axis of the articulator addition the marking mechanisms are arranged which can eventually be adjusted with length marked needles exactly to the rotation center.

A further especially preferred embodiment is characterized in that for the head-related incorporation of jaw models the rectangularly arranged side arms of the orientation arc feature each a marking mechanism which is movable and fixable in the direction of the parallel to each other arranged side arms of the orientation arc.

A further especially preferred embodiment is characterized in that for the head-related incorporation of jaw models the marking mechanisms with, for example, four-edged profile formed side arms of the orientation arc is formed as a carriage which is fixable by means of a fixation screw and accepts rectangularly to its direction movably a needle which preferably can be directed towards the rotation center of the respective articulator with spring tension exactly horizontally and reproducibly.

A further especially preferred embodiment is characterized in that the model plate for the secure reponability of taken jaw models carries a positive or negative relief (split cast relief).

In a further especially preferred embodiment there is in the model plate a magnet in an iron inset removably set in. The holding of the placed model takes place via a small iron plate which was beforehand fixed thereto by means of gypsum.

A further especially preferred embodiment is characterized in that in the model plate an iron plate is worked in, which forms the bottom of a magnet acceptance and forms with the brought in magnet, which is surrounded via a glue-joint by an iron ring, a loosenable magnet pot system, whereby the iron ring to the iron plate features a face which corresponds with a corresponding face of the magnet acceptance and thereby assures a position definition of the magnet and its taking out from the magnet acceptance of the model plate is made possible in that an iron core equipped with a holding grip or the magnet side without face of the iron ring set up effects an increased adhesive force.

In an especially preferred embodiment an iron core is set into the model plate, wherein a magnet is put into the model by means of gypsum.

A further especially preferred embodiment is characterized in that the model plate on the side opposed to the model features positive retentions like protrusions, threads with screws or the like or negative and hollow retention elements like recesses or millings for the connecting medium between model plate and articulator base plate.

A further especially preferred embodiment is characterized in that for the retention for the connecting medium screws are utilized which are preferably formed as countersunk screws through the model plate and are connected to nuts on the side opposed to the model and in such a way provide a separation of the model plate from the compound whereby the model plate on the side opposed to the model is equipped with guidance pads or recesses which allow a secure repositioning into the system.

A further especially preferred embodiment is characterized in that the articulator mounting plate in the central area are adjusted to the respective articulator type by means of threads and millings.

A further especially preferred embodiment is characterized in that the articulator mounting plate, moved from the articulator specific threads and millings, also features retention places for the connecting medium which on the model side are hollow recesses or conical borings and which are arranged in such a manner that the retention elements of the model plate interact without disturbance with those and that also in the case of a necessary special change of the model plate no influencing of the retention elements takes place.

A further especially preferred embodiment is characterized in that the articulator mounting plate is available in different strength or that for the special covering of distance between model plate and articulator mounting plate distance plates or frames are utilized which minimize the connecting joints.

A further especially preferred embodiment is characterized in that for the determination of the imaginary rotation axis of arcon-articulators which feature as artificial jaw hinge heads on the articulator columns each a ball calotte, whereby the rotation axis runs to the center of the ball, an auxiliary mechanism is utilized which processes via a transverse connection to opposingly mounted screw elements, which are flush with each other and formed in such a manner that they are for the setting of the hinge ball negatively conically or calottewise milled are via a threaded part and guidance part in their longitudinal direction variably and on the transverse connection movably mounted and indicate at their outer side point-like the turning center of the rotation axis.

With the help of these enclosed figures, which show particularly preferred examples of the invention, the latter is now explained in more detail.

BRIEF DESCRIPTION OF THE DRAWINGS

FIG. 20 is an enlarged view of the loosenable magnet pot system;

FIG. 21 is a view of the model plate, taken from the articulator side;

FIG. 22 is a top view of a variant of the mounting plate as seen from the model side;

DETAILED DESCRIPTION OF THE PREFERRED EMBODIMENTS

Figure 1:
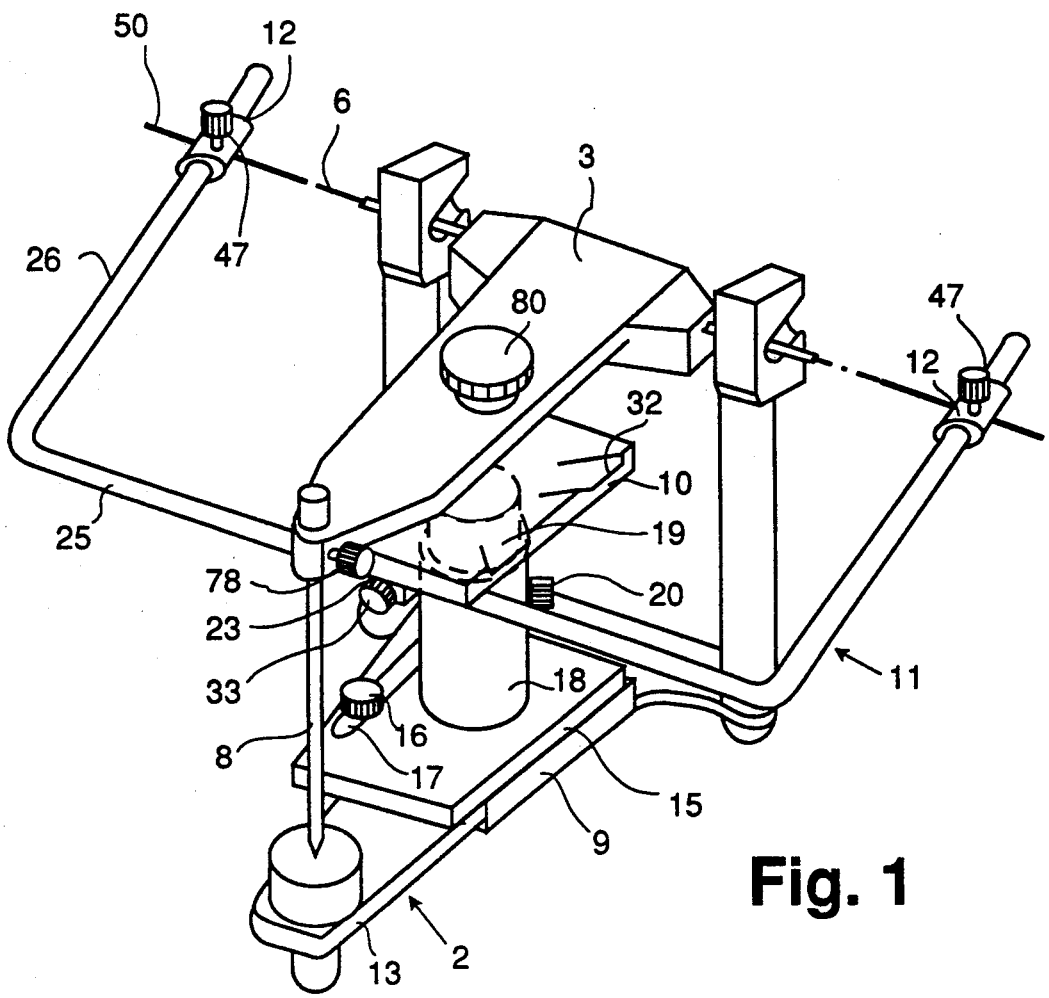
FIG. 1 is a perspective view of an apparatus according to a first preferred embodiment of the present invention, showing a common articulator model.

FIG. 1 shows a perspective view of the apparatus according to the invention in a common articulator 2, whereby a carrier plate 10 is shown in a transparent way and a negative split cast relief 32 is only indicated. An articulated base plate 9 is connected to and slidably supports a ground plate 15, which is positionally fixed via a set screw 16, whereby the ground plate 15 can be moved forwardly, towards the anterior, of articulator 2 via a slot 17. A cylinder 18 is mounted on the ground plate 15 and a shaft which mounts a carrier plate 10 is fixed via a set screw 20. An orientation are 11 has a transverse arm 25 and four-edge side arms connected to each end of transverse arm 25. Transverse arm 25 is slidably mounted in a holding element 23 which is fixedly connected to the carrier plate 10. The position of the orientation arc 11 is fixed via a set screw 33 after a desired position is achieved by sliding and rotational movement in the guidance hole 24 (FIG. 5) of the holding element 23, so that a marking mechanism 12 of the orientation arc 11 indicates on both sides symmetrically and in the same distance onto the rotation axis 6 of the articulator 2.

Thereby, a pointed pin 8 of the articulator 2 is brought by means of a set screw 78 into a vertical null-position. In a preferred embodiment the adjustment of marking mechanisms 12 of the orientation arc 11 is made easier by needles 50, which feature for symmetrical arrangement a graduation. The anterior position, of ground plate 15 may be necessary in a case for example, there the head-related upper jaw position, is taken from another articulator type, and is to be transpositioned to the articulator 2 of the type presently shown.

Figure 2:
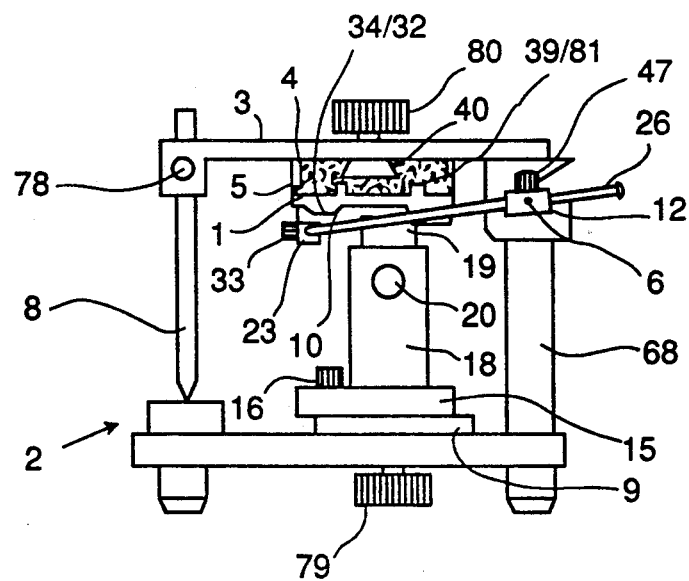
FIG. 2 is a side view of a mounted apparatus according to the invention of FIG. 1.

FIG. 2 shows a side view of the apparatus according to the invention. Articulator base plate 9 is mounted via a set screw 79. The ground plate 15 is illustrated moved to the anterior and fixed via the set screw 16. Due to the position of the piston 19 in the cylinder 18 and the aforementioned anterior position of the ground plate 15, the marking mechanism 12 of the orientation arc 11 is on both sides symmetrically arranged towards the rotation center 6 of the articulator 2. FIG. 2 exemplifies the incorporation of a split cast plate 1 around the articulator 2 with reference to the head-related upper jaw incorporation with another articulator type to be synchronized.

The figure shows how split cast plate 1 with its relief 34 exactly fits into the relief 32 of the carrier plate 10 and how in the position achieved the connection between split cast plate 1 and an upper jaw articulator mounting plate 4, which was premounted by set screw 80 of the articulator 2, is created.

A connecting medium 5 preferentially gypsum, plastic or similar materials are utilized. The retention takes place via retention protrusions 39 of split cast plate 1 and undercuts 40 of the upper jaw mounting plate 4.

Figure 3:
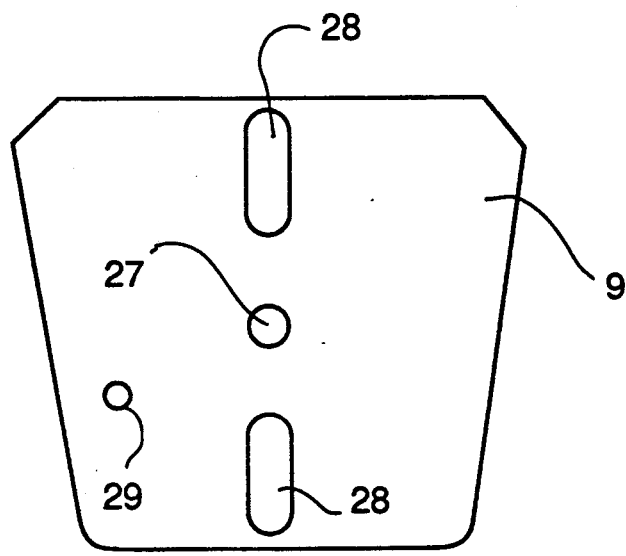
FIG. 3 is a top view of an articulator base plate according to the present invention.

FIG. 3 shows a top view of the articulator base plate 9, in which an articulator-specific threaded bore 27 and articulator-specific openings 28 serve for mounting into the respective articulator. Threaded bore 29 engages the set screw 16 to effect change of position of the ground plate 15

Figure 4:
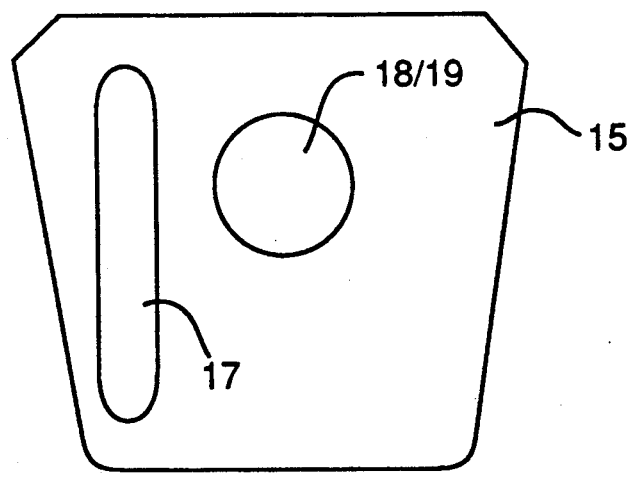
FIG. 4 is a top view of a ground plate showing a surface opposed to the articulator base plate, whereby the position of a mounted sleeve 18 or a mounted round rod 19 are only sketched.

FIG. 4 is a top view of the ground plate 15, whereby the slot 17 allows sliding movement of the ground plate 15 relative to the articulator base plate 9, whereby at the same time the diameter of the slot 17 is such that, when the set screw 16 is loosened, a small bodily side movement of the ground plate 15 is made possible. The position of the cylinder 18 or the shaft 19 is also indicated.

Figure 5A:
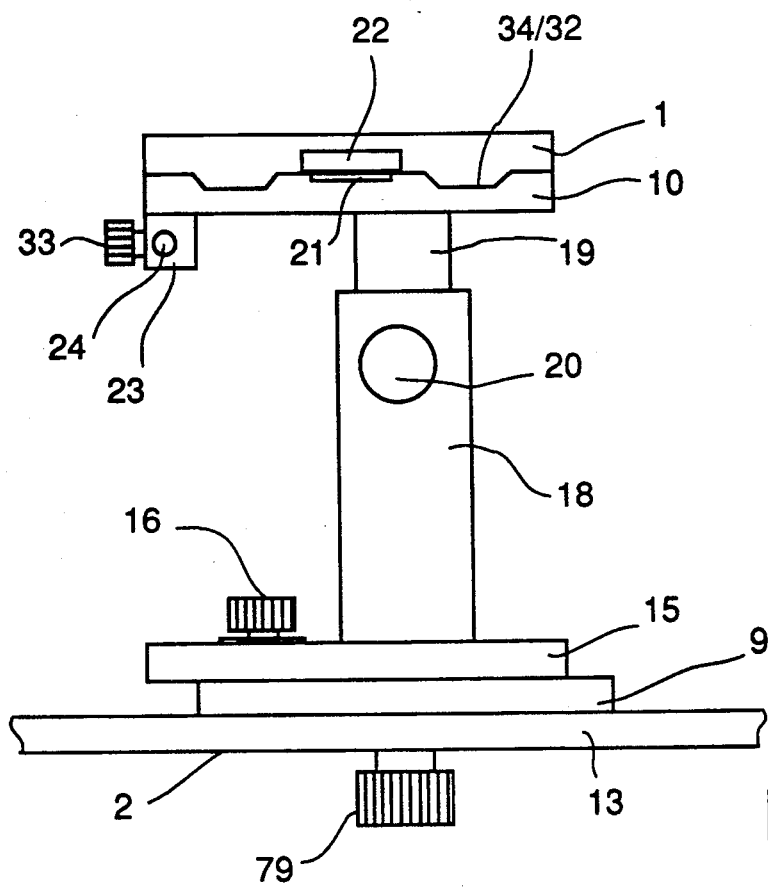
FIG. 5(a) is a side view of the apparatus according to the invention.

FIG. 5(a) is a side view of the apparatus according to the invention whereby the articulator 2 is visible only partially with the set screw 79. Here also is featured the anteriorly moved position of the ground plate 15 as compared to the articulator base plate 9 with the set screw 16. The shaft or piston 19 is positionally fixed in the cylinder 18 by means of the set screw 20. On the carrier plate 10 split cast plate 1 grips flush whereby in this preferred embodiment the mutual holding of the plates is assured via small iron plates 21 in the carrier plate 10 and magnet 22 in the split cast plate 1. The reversed variant, whereby the magnet 22 is anchored in the carrier plate 10 and the split cast plate 1 carries an iron core, can be used.

FIG. 5(a) also shows the fixed holding element 23 which accepts in its guidance hole 24 the orientation arc 11 with its transverse arm 25.

Figure 5B:
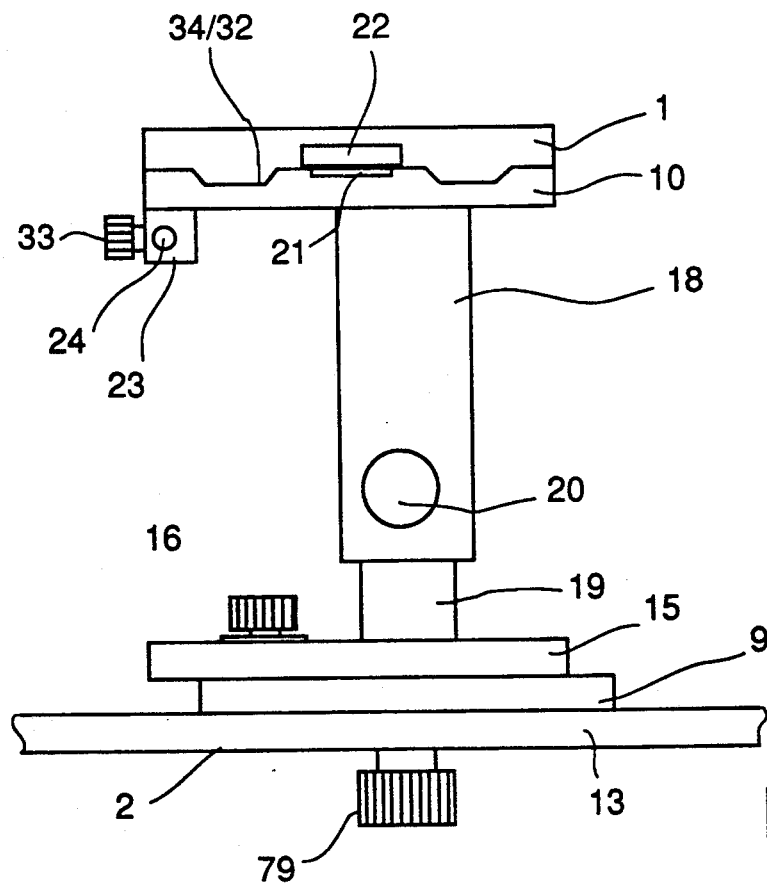
FIG. 5(b) is a variation of FIG. 5(a)

FIG. 5(b) shows a variant of the previously described apparatus according to the invention whereby as an alternative the shaft 19 is mounted on the ground plate 15 and the cylinder 18 is movable vertically and axially and can be positionally fixed via the set screw 20.

Figure 6:
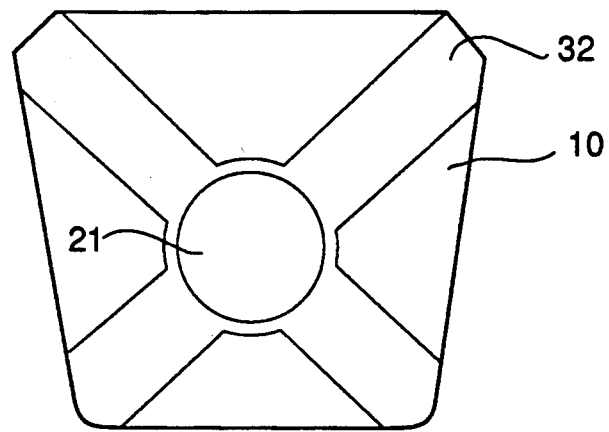
FIG. 6 is a top view of a carrier plate of the present invention.

FIG. 6 is a top view of the carrier plate 10, which carries in the central area a small iron plate 21 and is suitable together with a negative split cast relief 32 for the exact repositioning of the split cast plate 1 over the split cast relief 34.

Figure 7A:
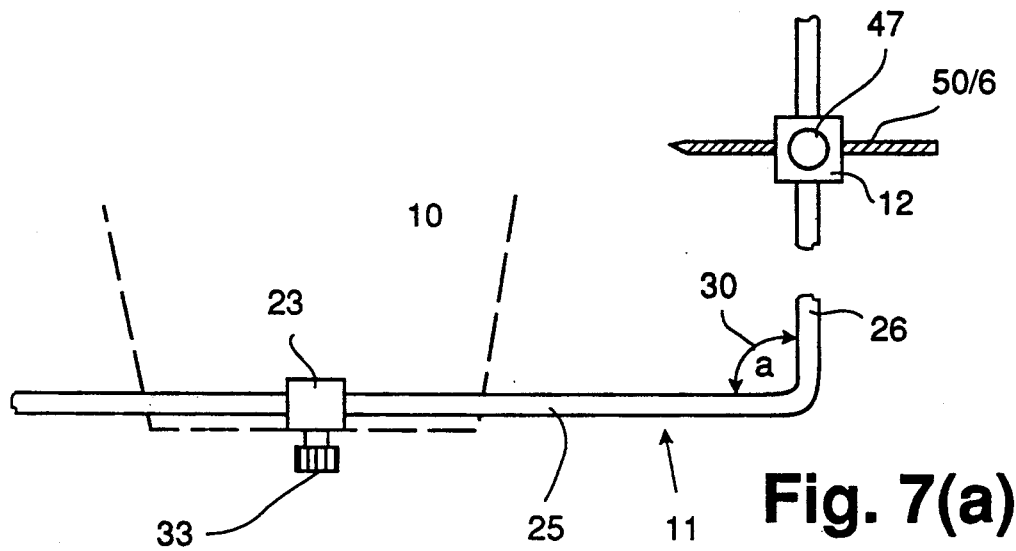
FIG. 7(a) is a detailed view showing an orientation arc.

FIG. 7(a) shows in a detailed view the orientation arc 11, which is fixed by the set screw 33 in the holding element 23.

The carrier plate 10 is shown in the drawing by phantom or dashed lines. Also, FIG. 7(a) shows a top view of the marking mechanism 12, which is positionally fixed by means of the set screw 47 at the orientation arc 11 and which accepts in a preferred embodiment a marking needle 50 which is graduated to facilitate a symmetrical arrangement.

Figure 7B:
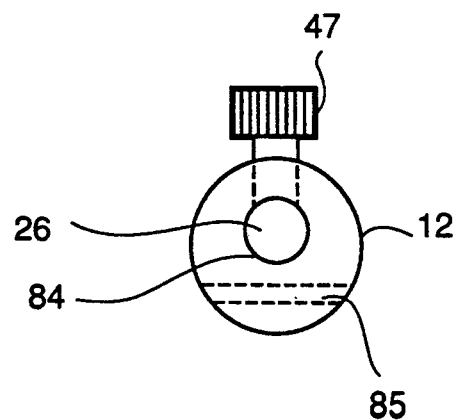
FIG. 7(b) is a detailed front view of the marking mechanism of the orientation arc.

FIG. 7(b) shows in detail the marking mechanism 12 in a front view whereby at the set screw 47 the marking mechanism 12 is positionally fixed relative to the side arm 26 of the orientation arc 11.

Below the base 84 which slidably receives the side arm 26 of the orientation arc 11 is presented a smaller bore 85 which receives the marking needle 50.

Figure 8:
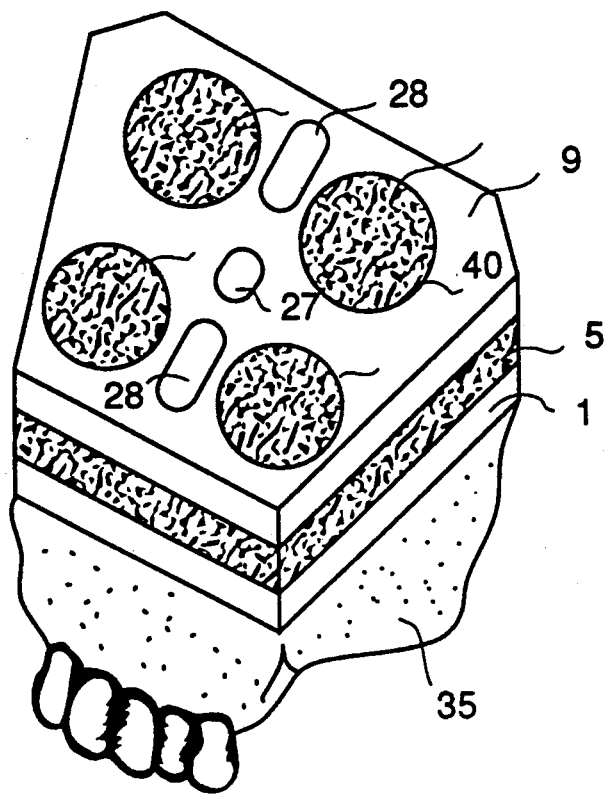
FIG. 8 is a perspective view of a portion of the apparatus according to the present invention, without the articulator.

FIG. 8 shows a perspective view of the apparatus according to the invention without the articulator 2. The central threaded bore 27 secures the base plate 9 to the articulator 2 by means of the set screw 80. The openings 28 fix the articulator base plate 9 stably against rotation in the apparatus. In the conical borings 40 which feature the small diameter towards the articulator side the holding medium (gypsum, plastic, or others) 5 is visible. This holding medium 5 is also present between the articulator base plate 9 and the split cast plate 1. The split cast plate 1 carries a jaw model 35.

Figure 9:
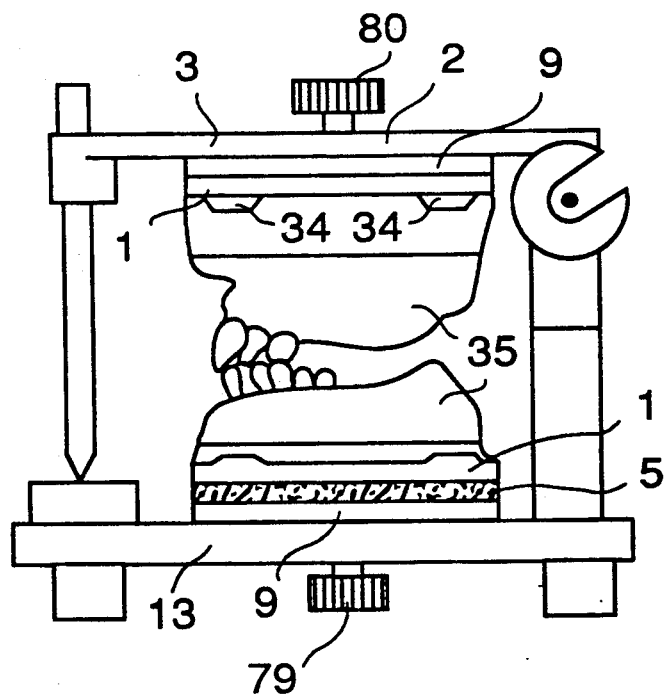
FIG. 9 is a side view of the apparatus on a common articulator mode.

FIG. 9 is a side view of the mounted apparatus on a common articulator model 2. The articulator base plate 9 is mounted via a set screw 80/79 on the articulator 2. The holding medium 5 fixes the split cast plate 1 at the articulator base plate 9. The model 35 is added onto the split cast plate 1. FIG. 9 illustrates the relations in the area of the upper jaw 3- as well as in the area of the lower jaw 13-articulator arm.

Figure 10:
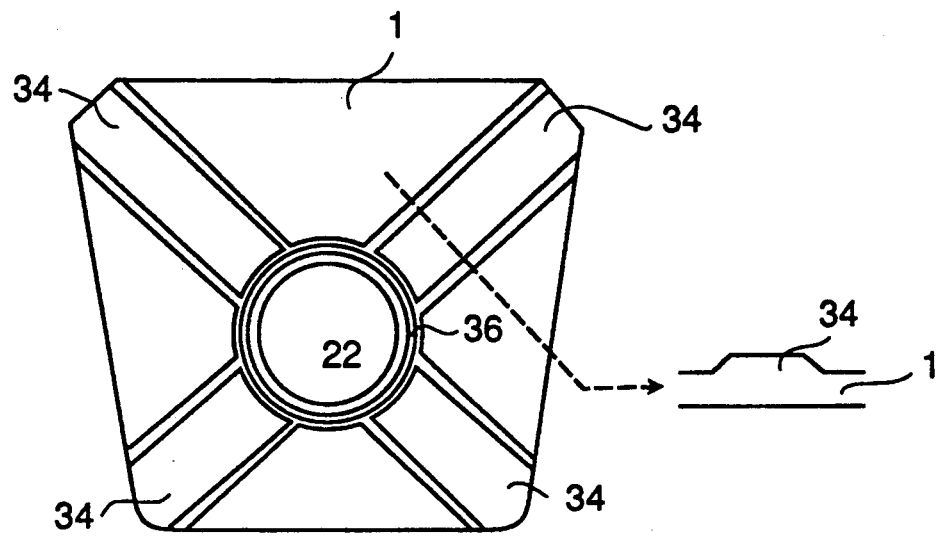
FIG. 10 is a side view of the split cast plate, taken from the model side.

FIG. 10 shows the split cast plate 1 from the model side (the side on which model 35 is placed). A negative or positive re-lief (split cast relief) 34 guarantees exact repositioning of removed gypsum models 35. The holding of these gypsum models 35 is assured via a magnet 22 which is fixed in the split cast plat 1 via an iron insert 36 by magnetic force of a removable manner.

Figure 11:
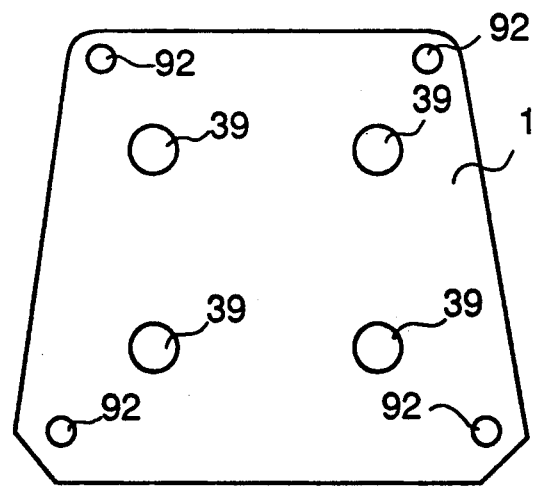
FIG. 11 is a side view of the split cast plate, taken from the articulator side.

FIG 11 shows the split cast plate 1 from the articulator side. Retention elements 39 such as protrusions, threads or screws or recesses are visible. Moreover, retention elements 92 interact in the starting position exactly into corresponding retention elements 39 of articulator base plate 9. The retention elements 39 lie in the starting position preferably centrally in the retention recess 40 of articulator base plate 9.

Figure 12:
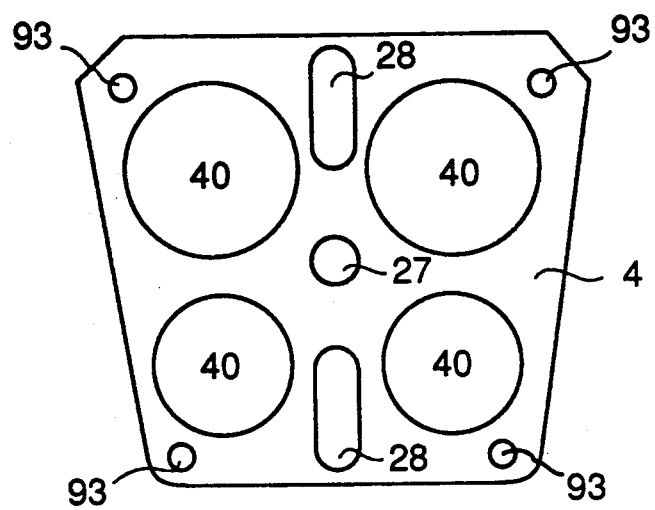
FIG. 12 is a side view of the articulator base plate, taken from the model side.

FIG. 12 shows the articulator base plate 9 from the model side. The articulator specific threaded bore 27 and the articulator specific opening 28 can be seen.

The preferred conical retention recesses 40 for receiving the connecting medium 5 or for the interaction of the retention protrusions 39 feature on the model side the smaller diameter. Moreover, retention elements 39 interact in the starting position exactly into the corresponding retention elements 92 of split cast plate 1.

Figure 13:
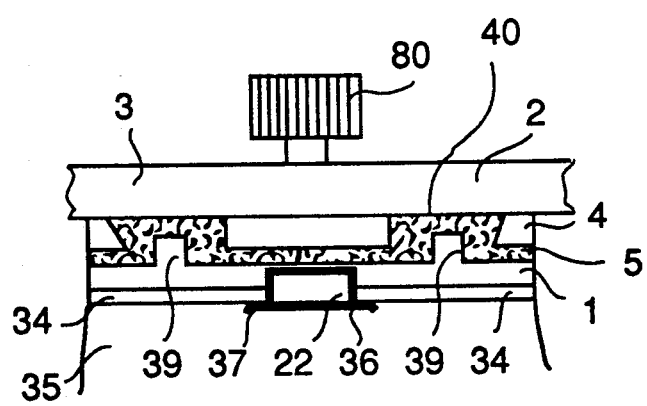
FIG. 13 is a cross section through the mounted apparatus with added holding medium.

FIG. 13 shows a cross-section through the mounted kit. In articulator 2, the articulator mounting plate 4 is mounted above the holding screw 80. The crosssection opening of bore 27, specific openings 28 and retention elements 92 are not shown in FIG. 13. The retention recesses 40 which interact with the retention protrusions 39 of split cast plate 1, whereby the holding medium 5 fixes the split cast plate 1 to the articulator mounting plate 4. Relief 34 serves for the positioning of model 35 which adheres via a gypsum fixed small iron plate 37 at the magnet 22 of split cast plate 1. The holding of magnet 22 to split cast plate 1 itself again is assured by means of an iron insert 36.

Figure 14:
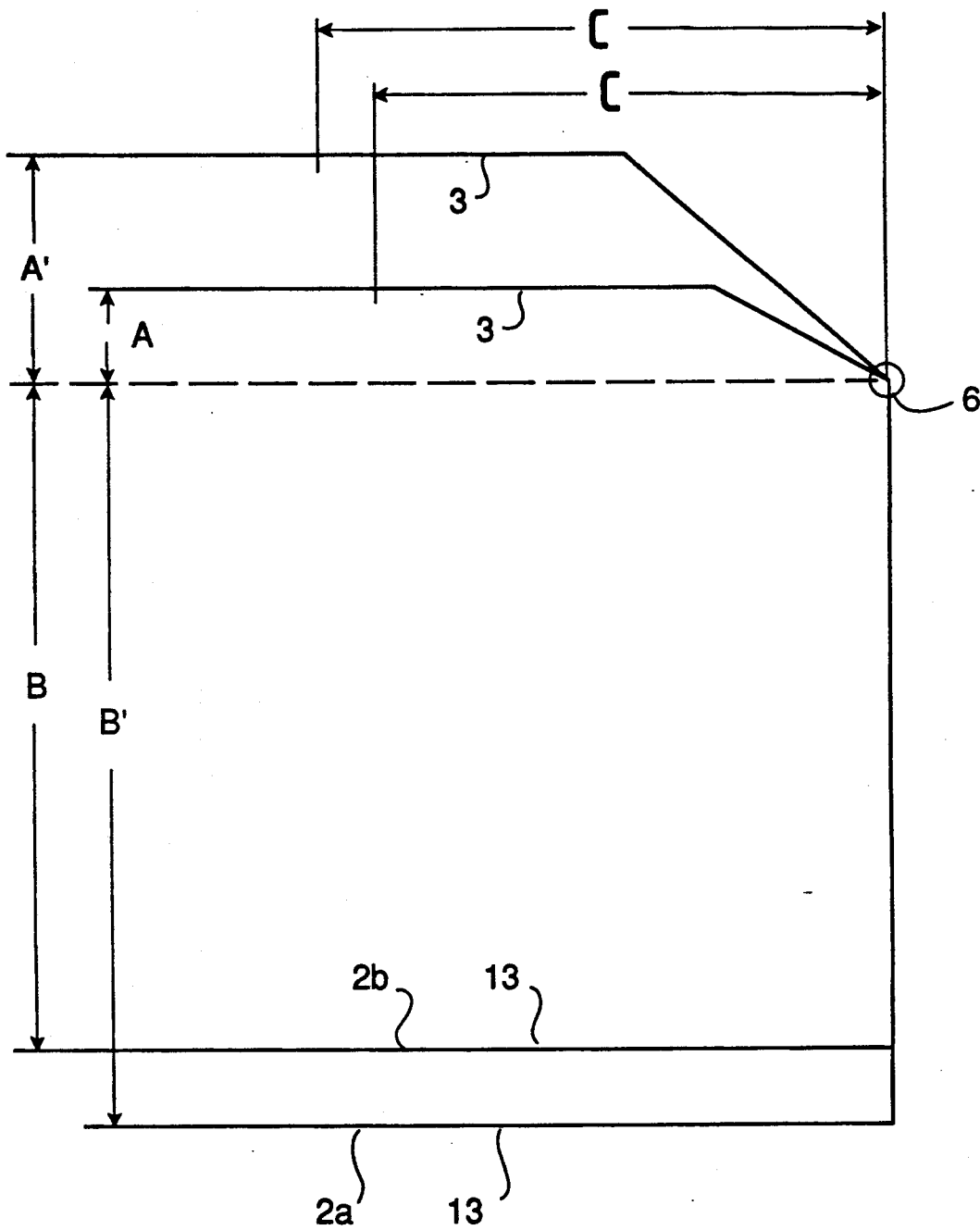
FIG. 14 is a schematic view of two sketched articulators, showing the important minimal distances.

FIG. 14 indicates two sketched articulators 2a, 2b of different building height, whereby the letters A, A' represent the vertical distance between the articulator upper jaw arm of the articulators 2a, 2b and the rotation axis 6 of both apparatuses. Similarly, the letters B, B' indicate the vertical distance between the articulator lower jaw arms 13 and the common rotation axis 6.

Figure 15:
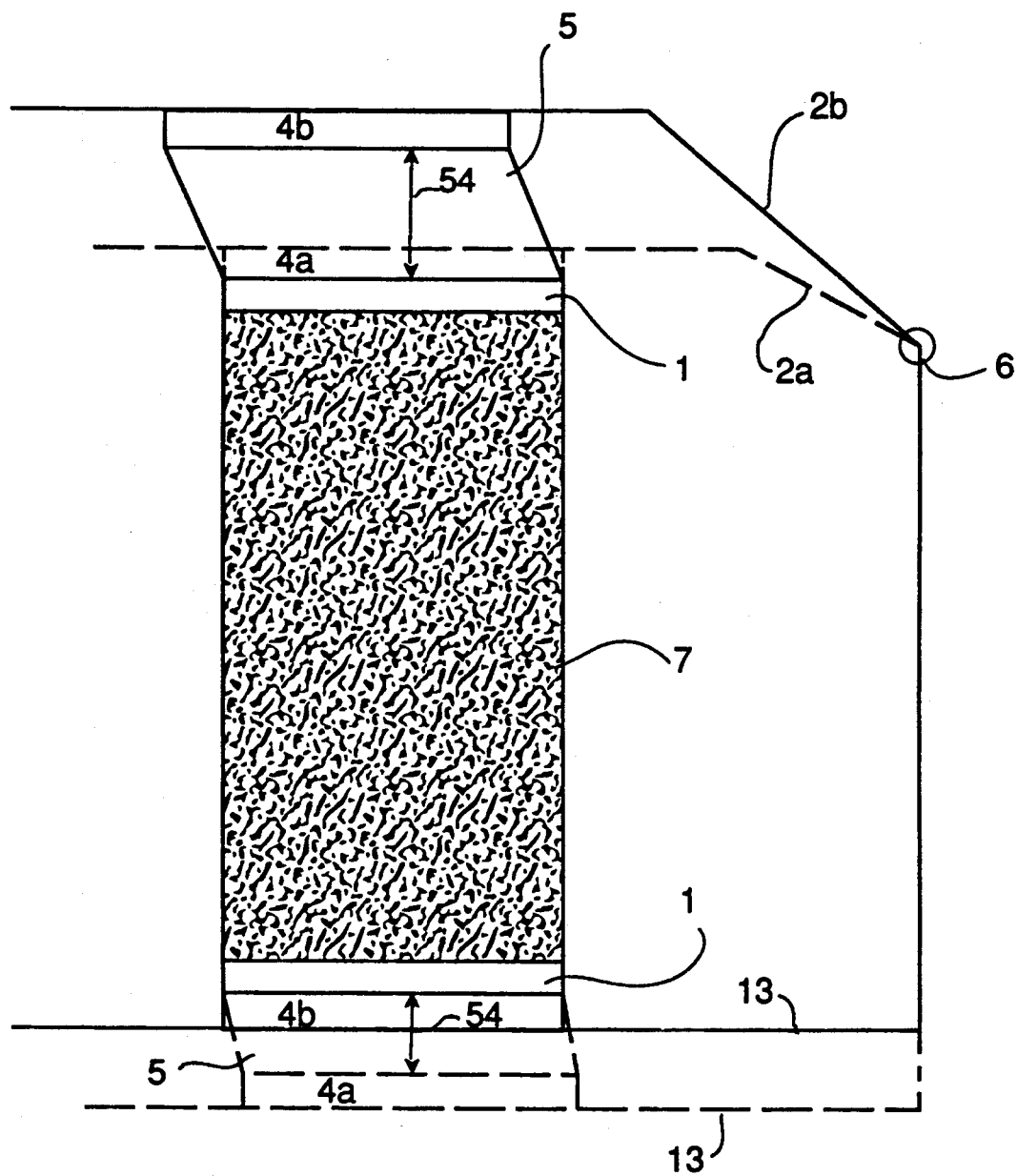
FIG. 15 is a schematic view of two sketched articulators with the insert of a central relation block for the incorporation of the lower split cast plates with adjusted upper jaw split cast plates.

FIG. 15 shows schematically articulators 2a, 2b and the incorporation of a central relation block 7 for the incorporation of the lower jaw split cast plates 1. Both articulators 2a, 2b carry in above-each-other projection their respective upper jaw split cast plate 1 in identical spatial relation to the perspective rotation axis 6, in which they are connected via the intermediate medium 5 with their respective mounting plates 4a and 4b separated by a distance 54 4.

The central relation block 7 serves for the incorporation of the lower jaw split cast plate 1, whereby first the mounting at smallest distance B (see FIG. 14) from articulator lower jaw arm 13 to rotation axis 6 was carried out and subsequently via the connecting medium 5 the mounting of the lower jaw split cast plate 1 of the second articulator 2a with its corresponding mounting plate 4a was carried out.

Figure 16:
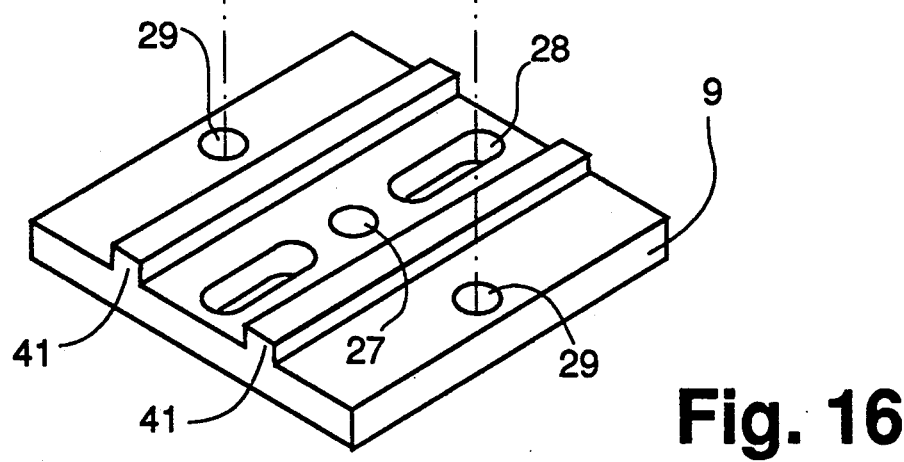
FIG. 16 is a perspective view of an articulator base plate with a guidance relief, parallel to the articulator specific threads and millings.

FIG. 16 is a perspective view of a differently formed articulator base plate 9, wherein guidance reliefs 41 are arranged in parallel to the articulator specific threaded bore 27 and the openings 28, which serve for the guidance of the ground plate 15 in the longitudinal direction. At the same time it becomes evident that for the secure fixing of the ground plate symmetrically, two threaded bores 29 are provided.

Figure 17:
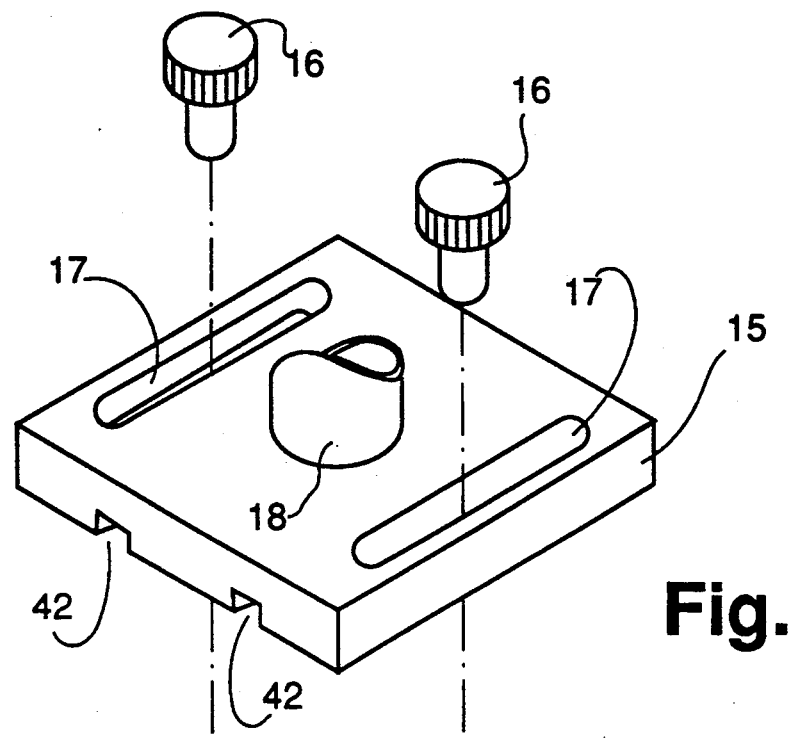
FIG. 17 is a perspective view showing the base plate taken from the side opposed to the articulator base plate.

FIG. 17 is a perspective view of the ground plate 15 from the side opposed to the articulator base plate 9, wherein the position of a mounted guidance sleeve 18 is illustrated. In the present embodiment, longitudinal sliding movement of ground plate is assured by guidance relief 42, which corresponds with the guidance relief 41 of the articulator base plate 9. The longitudinal movement itself is limited by the length of the two slots 17, by means of which two set screws 16 engage the threaded bores 29 of the articulator base plate 9 and fix the ground plate 15.

Figures 18, 19:
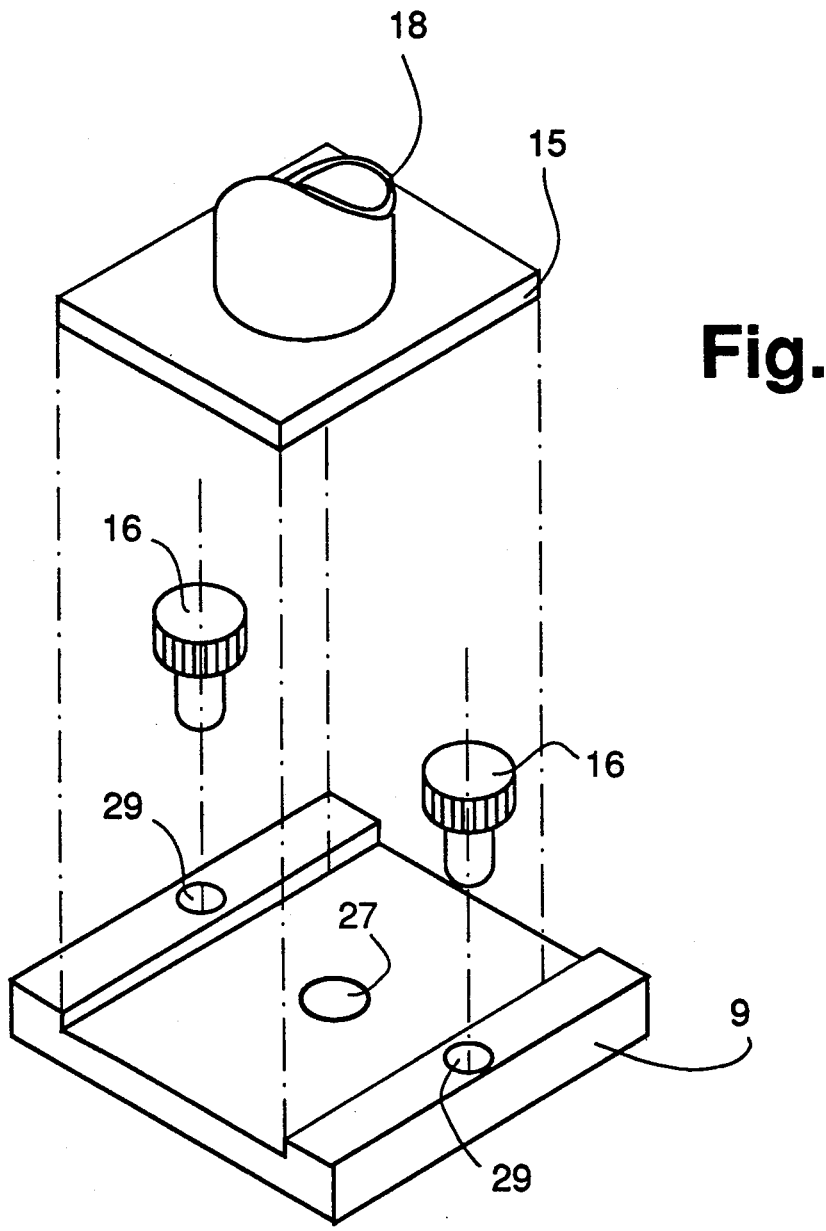
FIG. 18 is an exploded view of an articulator base plate.
FIG. 19 is a top view of the split cast plate with integrated magnet and countersunk screws, taken from the model side.

FIGS. 18 and 19 show an additional variant of the articulator base plate 9 and the correspondingly executed ground plate 15. In this embodiment the articulator base plate 9 is U-shaped and the ground plate 15 is corresponding to the articulator base plate 9 executed in such a way that this is guided within the U-shaped form. Fixation takes place via the screws 16 disposed on both sides.

FIG. 20 is a top view of the split cast plate 1 showing cross-like arranged positive guidance pads 34, which draw onto the added model 35 a corresponding split cast relief and serve to ensure the exact respositioning and stability of the model 35 position. A magnet 22 with iron ring 62 is located centrally within a magnetic acceptance 60 of the split cast plate 1, whereby the connection of magnet 22 to iron ring 26 is carried out by means of a plastic glue joint 61. It is to be emphasized that the magnet 22 in the form presented in the magnetic acceptance 60 is arranged under level so that upon withdrawing of a model set up there which carries for holding of the model a small iron plate 37, the magnet 22 remains in the magnet acceptance 60 in such a fashion that the bottom of the magnetic acceptance 60 in the split cast plate 1 is formed as a small iron plate 59 to which it directly adheres and thus forms a loosenable magnetic system, whereas it is arranged towards the small iron plate 37 of model 35 at a distance so that the magnetic flux experiences a weakening in this case. The split cast plate 1 furthermore shows in the presented case symmetrically arranged bores 87 for the acceptance of preferable countersunk screws 55 which form together the backsidedly arranged hollow nuts 56 retentioned positions for the connecting medium 5.

FIG. 21 again explains in a detailed view the loosenable magnetic system whereby in the side view it can be seen that the magnet 22 is surrounded via a glue joint 61 with an iron ring 62 which features a face 63 and lies on a small iron plate 59 which is indicated in the corresponding recess of the split cast plate 1. The face 64 of a magnet 22 again corresponds to a corresponding face of the magnetic acceptance 60 of the split cast plate 1 so that magnet 22 cannot be positioned with the wrong side in the magnetic acceptance. FIG. 21 furthermore exemplifies how the removal of the magnet 22 from the magnetic acceptance 60 can be carried out. The magnet lifter 65 shown above the magnetic system is directly positioned onto the magnet 22 in its magnetic acceptance with its iron core 66 which corresponds in the outer diameter to the iron ring 62, so that now due to the ring face 63 bying on the small iron plate 59, an increased magnetic flux is created and thus the magnetic system is made loosenable.

FIG. 22 is a top view onto the split cast plate 1 from the articulator side. Moreover, this view shows a negative guidance relief 58, which allows after loosening of the split cast plate 1 by removal of the screws 55 a removal and secure repositioning of the split cast plate 1.

Figure 23:
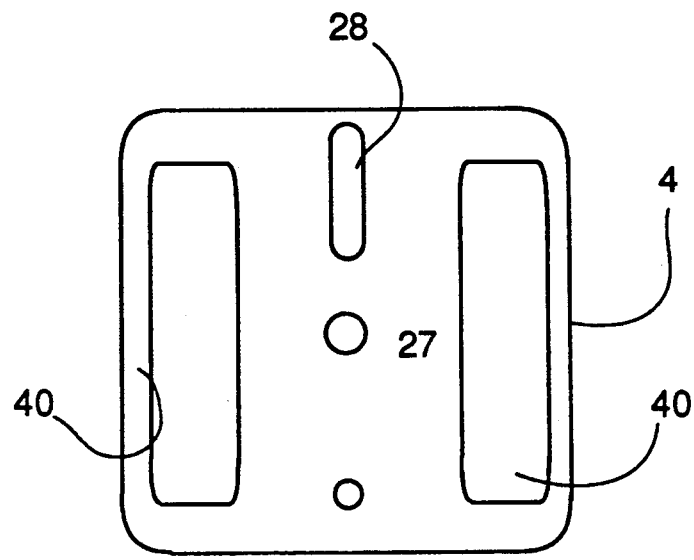
FIG. 23 is a detailed view of the connection model plate/mounting plate via screw and retention nut and a connecting medium in joint.

FIG. 23 is a top view of the mounting plate 4 from the split cast plate 1. In the middle part the articular specific threaded bore 27 and opening 28 are recognizable. The retention 40 are symmetrically arranged in the longitudinal direction in the form of elongated openings which moreover form towards the split cast plate 1 an undercut so that the added connecting medium 5 towards the model side in the adjusted condition cannot be removed.

Figure 24:
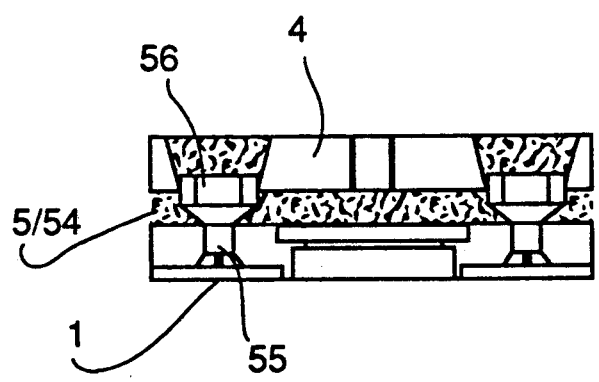
FIG. 24 is a view of the carrier plate with mounted orientation arc.

FIG. 24 shows in cross-section a detailed view of the connection split cast plate 1/mounting plate 4 via the screws 55 and retention nuts 56, with the preferably utilized connecting medium 5 having a connecting joint 54.

Figure 25:
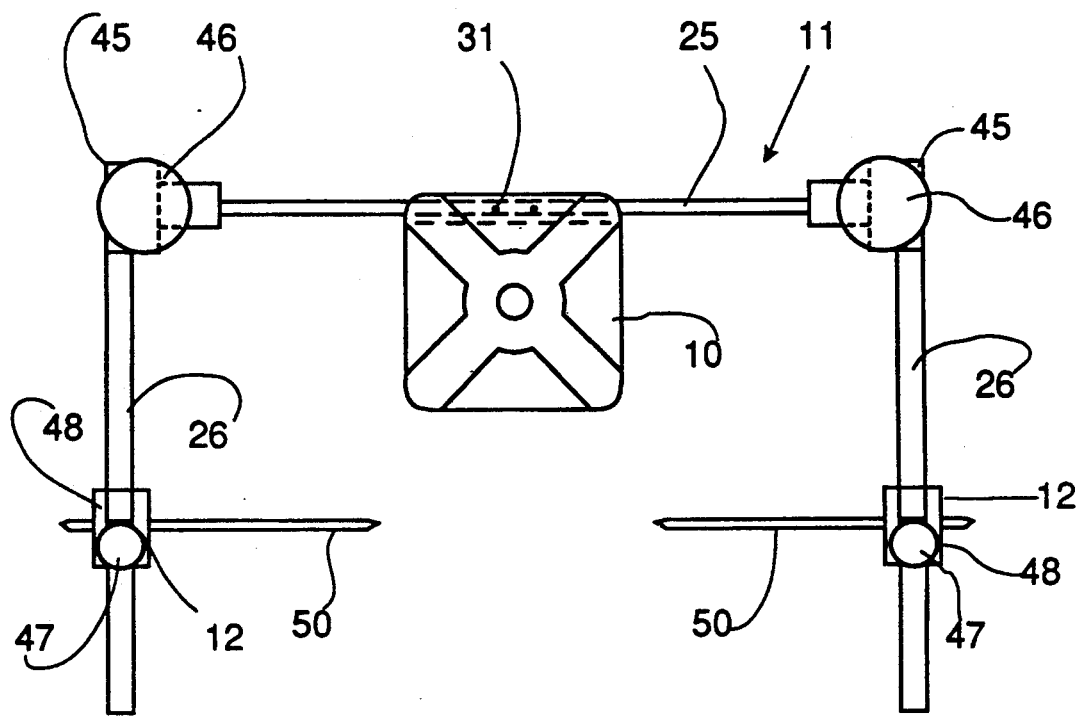
FIG. 25 is a perspective view of a marking mechanism with spring tension marking needle.

FIG. 25 shows in simple form an elevational view onto the carrier plate 10 with mounted orientation arc 11 which is fixed with its transverse part 25 via the set screws 31. The figure shows furthermore both four edged side arms 2 arranged with marking mechanisms 12, marking needles 50 and set screws 47.

Figure 26:
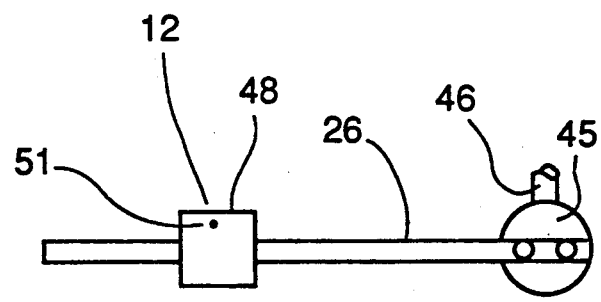
FIG. 26 is a side view of FIG. 25 showing rotatably and fixably arranged four-edge side arm and marking mechanism.

FIG. 26 shows in side-view a detail of FIG. 25 with rotatably arranged four-edged side arm 26, whereby here preferably transverse arm 25 is made of round material and solidly fixed. The connection of the four-edged side arm 26 via the transverse arm 25 takes place by means of a hinge connection 45 which is fixed via the set screw 46 in the adjusted condition.

Figure 27:
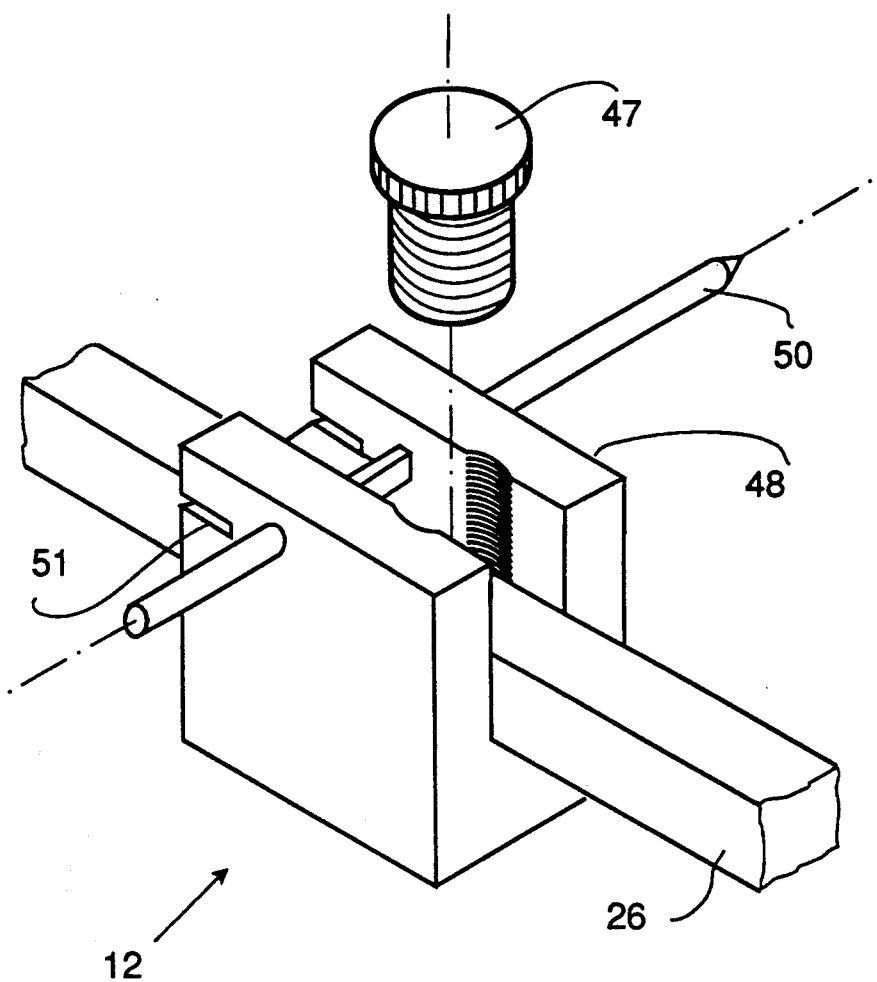
FIG. 27 is a perspective view of an auxiliary mechanism for finding the hinge axis with arconarticulators.

FIG. 27 is a detailed perspective view of the removable marking mechanism 12 on the four-edged side arms 26, which is formed like a carriage. The set screw 47 fixes its position. Marking needles 50, which are under spring tension 51, provide exact horizontal positioning.

Figure 28:
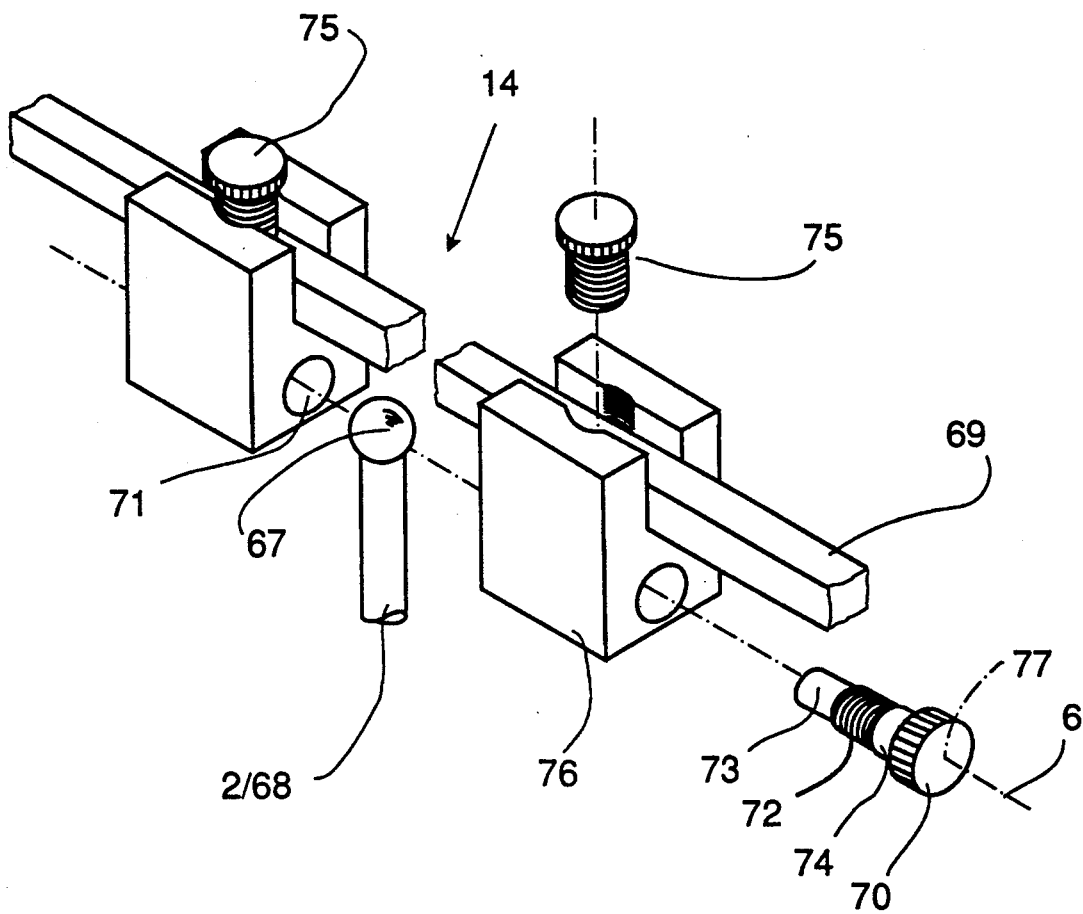
FIG. 28 is a perspective view of another form of the sleeve arranged on the articulator base plate or on the ground plate and round rod.

FIG. 28 shows a perspective presentation of an auxiliary mechanism 14 for finding the hinge axis 6 with arcon articulators. With these apparatuses, the imaginary rotation axis runs through the center of the artificial jaw hinge heads, which are formed as ball joints 67 (only one ball joint 67 is indicated). The auxiliary mechanism 14 connects via a preferably utilized four-sided transverse connection 69 to opposingly mounted screw elements 70 which are exactly flush with each other and are formed in such a way that for the positioning of the ball joints, negatively conical recesses 71 are formed in a shape corresponding to the ball joint. A thread part 72 and guidance part 73/74 are provided in the longitudinal direction in a carriage-like movable block 76 variably mounted, which again is movable on the transverse connection 69 and can be fixed via set screws 75. Moreover, the screw elements 70 have a common rotational axis 77 which corresponds to the rotation center 6.

Figure 29:
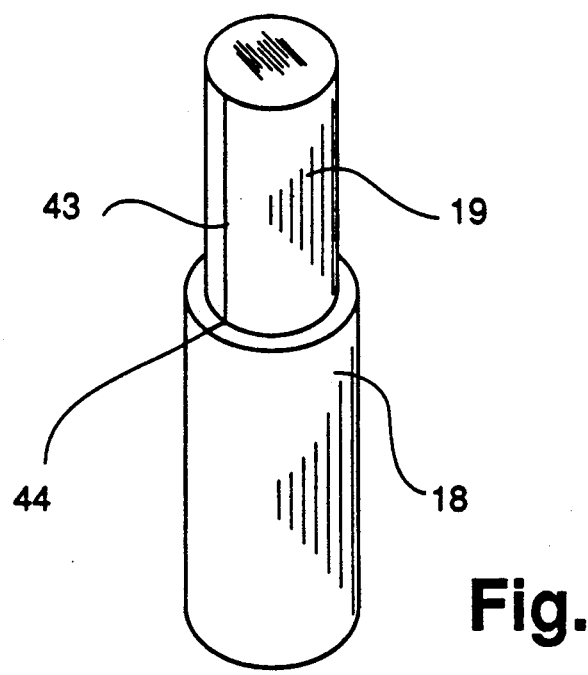
FIG. 29 is schematic view showing the distance plates of the frame functioning for special disturbance compensation between split cast plate and articulator mounting plate 4.

FIG. 29 shows a further embodiment of the cylinder 18 arranged on the ground plate 15 with the piston 19. In this exemplary embodiment for the head-related incorporation of a jaw model at the exactly fittingly-made inner piston 19 in exactly vertical direction a marking 43 is arranged on inner piston 19 which corresponds with the second marking 44 on the outer cylinder 18 and which enables to fix the direction of angular orientation of the piston 19 with the mounted carrier plate 10 with single arrangement of cylinder 18 and piston 19.

Figure 30A:
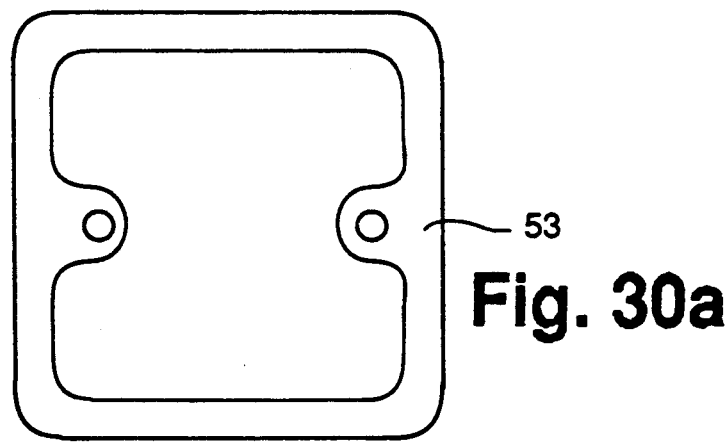
FIG. 30 is a top view showing the distance plates for the special covering of the distance between the split cast plate and the articulator mounting plate.
Figure 30B:
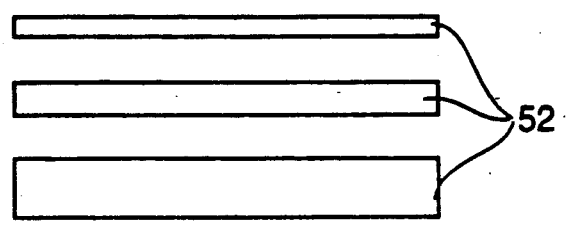

FIG. 30 shows the distance plates 52 of frame 53 functioning for the special covering of distance between split cast plate 1 and articulator mounting plate 4 which minimizes the connecting joint 54 for the connecting medium 5.

What is claimed is:

1. A method for synchronizing a hinge axis and centric relation-block of unequally constructed articulators, to facilitate the exchange of jaw models, comprising the steps of:
   (a) loosenably fixing identical first split cast plates in each of the unequally constructed articulators for synchronization of an articulator upper jaw arm to a specific mounting plate via a connecting medium in each of the unequally constructed articulators;
   (b) forming a concurring relation with respect to the hinge axis starting from a starting articulator having a position of each of the first split cast plates 1 which are optimally related to the hinge axis;
   (c) horizontally and vertically adjusting the hinge axis of the unequally constructed articulators to be synchronized; and
   (d) synchronizing the unequally constructed articulators by providing an identical spatial relation of second split cast plates using a centric relation block to form a correct connection with a lower jaw mounting plate of each of the unequally constructed articulators via the connecting medium.

2. A method according to claim 1, further comprising the step of utilizing an apparatus with a vertical minimal distance from the articulator upper jaw arm to the hinge axis with a pin position-0 as the starting articulator.

3. A method according to claim 1, further comprising the step of horizontally loosenably fixing the starting articulator and the first split cast plates with a pin-position-0 at the articulator mounting plate via the connecting medium.

4. A method according to claim 1, further comprising the step of operatively coupling an apparatus compatible articulator base plate to a parallel, vertically and horizontally movable carrier plate, which accepts in exact guidance using a relief the first split cast plates resulting in a concurrent special relation of the first split cast plates to the hinge axis at a pin-position 0 after synchronization.

5. A method according to claim 1, further comprising the steps of:
(e) adjusting an orientation arc and a marking mechanism, at the starting articulator to a position; and
(f) maintaining the position during synchronization of all of the unequally constructed articulators relative to a carrier plate.

6. A method according to claim 1, further comprising the step of utilizing an apparatus with a vertical minimal distance from an articulator lower jaw arm to the hinge axis as the starting articulator.

7. A method according to claim 1, further comprising the step of fixing a lower jaw split cast plate substantially horizontal with an equivalent articulator mounting plate in a loosenable manner.

8. A method according to claim 1, further comprising the step of finding an imaginary hinge axis with an auxiliary axis when the unequally constructed articulators include ball joints.

9. An articulator apparatus for center-related synchronizing a hinge-axis for incorporating unequally constructed articulators, comprising:
an articulator base plate;
a ground plate having a slot and upper surface, connectable to the articulator base plate via a screw and slidably disposed using the slot into which the screw is inserted;
a cylinder having a cylindrical cavity connected vertically to the upper surface of the ground plate;
a piston having an end and inserted in the cylindrical cavity and exactly guided in a vertical direction movably and telescopically and axially rotatably arranged, said piston fixable via a fixation screw;
a carrier plate connected to the end of the piston opposed to the articulator base plate,
a split case plate having top and bottom surfaces, said bottom surface provided with a magnet forming a magnetic connection with said countersunk iron plate, said split cast plate positioned on said carrier plate and exactly repositionable via the magnetic connection;
a fixation element connected to said carrier plate, which adjustably receives an orientation arc having a transverse part, side arms, and a marking mechanism adjustably connected to each of the side arms of the orientation arc, the orientation arc being adjustable to the hinge axis of the unequally constructed articulators using the marking mechanism; and
an articulator mounting plate supported by and connected to the split cast plate via a hardened viscous medium, said articulator mounting plate and said split cast plate being specially adjusted to each other via the hardened viscous medium.

10. An articulator apparatus according to claim 9, wherein the articulator base plate is provided with threaded bores and openings, which facilitate adjustable incorporation into the unequally constructed articulators, the articulator base plate further including a thread boring, which accepts the screw for fixing of the base plate.

11. An articulator apparatus according to claim 9, wherein the ground plate is provided with the slot which enables mobility of the ground plate on the articulator base plate when the screw is loosened.

12. An articulator apparatus according to claim 9, wherein at least one sleeve extends vertically on the ground plate, each accepting an exactly fitting piston which is telescopic, axially rotatable and fixable via a set screw.

13. An articulator apparatus according to claim 9, wherein on the ground plate at least one piston is arranged, over which vertically mobile exactly fitting sleeves in a single arrangement and axially rotatable are arranged slidably and in a fixable manner via a set screw.

14. An articulator apparatus according to claim 13, wherein the carrier plate having a side opposing a fixation is mounted on the vertically mobile exactly fitting sleeves, the side opposing the fixation including one of a negative and a positive relief, for accepting the split cast plate.

15. An articulator apparatus according to claim 9, wherein at least one profile is arranged on the ground plate upon which a second profile, exactly adjusted on the at least one profile is arranged vertically mobile and fixable.

16. An articulator apparatus according to claim 9, wherein the carrier plate has a countersunk small iron plate for fixing the split cast plate having the magnet.

17. An articulator apparatus according to claim 9, wherein the carrier plate has a carrier magnet for fixing the split cast plate to the carrier plate, the split cast plate having the countersunk iron plate.

18. An articulator apparatus according to claim 9, wherein a fixation element is arranged at the carrier plate, which fixes via a set screw the orientation arc, which has the of a transverse arm having ends connected to and in a same plane with the side arms.

19. An articulator apparatus according to claim 9, wherein the side arms of the orientation arc each include the marking mechanism which is mobile along the side arms of the orientation arc and fixable.

20. An articulator apparatus according to claim 9, wherein the split cast plate includes one of a negative and positive relief for taking-off and secure repositioning of a jaw model arranged with gypsum thereon.

21. An articulator apparatus according to claim 9, wherein the split cast plate includes an iron inset and is provided with the magnet, which is removably fixed in the iron insert by a magnetic force and which fixes a jaw model having a small iron plate arranged by means of gypsum via the small iron plate positioned on the jaw model by means of gypsum.

22. An articulator apparatus according to claim 9, wherein the split cast plate is provided with an iron jaw which fixes an added jaw model via a model magnet arranged thereon by means of gypsum.

23. An articulator apparatus according to claim 9, wherein the split cast plate includes a side opposite on its side opposing to model retention means for fixing fixation points with the connecting medium.

24. An articulator apparatus according to claim 9, wherein the articulator mounting plate includes threaded bores and openings, for incorporating different articulator types.

25. An articulator apparatus according to claim 9, wherein said split cast plate includes retentions, and
wherein the articulator mounting plate includes mounting threaded bores, mounting openings and retention places remote from the mounting threaded bores and mounting openings, said retention places including hollow recesses, positionally corresponding to the retentions, the retentions of the split cast plate in an initial starting position without disturbance interact with the retention places of the articulator mounting plate, and upon necessary special change of a position of the split cast plate, the retentions of the split cast plate and the retention places of the articulator mounting plate do not interfere with each other.

26. An articulator apparatus according to claim 9, wherein the ground plate includes one of a positive and negative relief and symmetrically arranged slots, and
wherein for head-related incorporation of jaw models the articular base plate includes parallel to the articulator specific openings, a threaded bore the one of the positive and negative relief, which corresponds with the one of the negative and positive relief of the ground plate the ground plate being only longitudinally slidable on the articulator base plate, and wherein a set screw fixedly connects the articulator base plate and the ground plate, the set screws being inserted in the symmetrically arranged slots of the ground plate and guided into the articulator base plate.

27. An articulator apparatus according to claim 9, wherein the cylinder includes a second marking, and
wherein for head-related incorporation of jaw models, the piston includes a marking formed in an exact vertical direction, which corresponds with the second marking of the cylinder for fixing the angular position of the piston.

28. An articulator apparatus according to claim 9, wherein for head-related incorporation of jaw models, the orientation arc is immobile and fixed by fixing the transverse arm with a set screw at the carrier plate, the orientation arc having the side arms arranged each via a rotatable hinge and via a set screw.

29. An articulator apparatus according to claim 9, wherein for the head-related incorporation of jaw models, the rectangularly arranged side arms of the orientation arc each include the marking mechanism which is mobile in a direction of the side arms of the orientation arc and fixable by means of a set screw.

30. An articulator apparatus according to claim 9, wherein for the head-related incorporation of jaw models, the marking mechanism includes a carriage, which can fixed by means of a set screw and accepts rectangularly to direction of movement of the marking mechanism a needle, which includes a spring horizontally and reproducible alignable towards the rotation center of the articulator.

31. An articulator apparatus according to claim 9, further comprising distance plates for closing a distance between the split cast plate and the articulator mounting plate which minimizes a connecting joint via the hardened viscous medium.

32. An articulator apparatus according to claim 9, wherein the split cast plate has a side opposite to a model inserted in the articular, and
wherein screws are provided for retention of the hardened viscous medium, the screws are countersunk through the split cast plate and are connected on the side opposite to the model with hollow nuts and allow the separation of the split cast plate a compound structure, whereby the split cast plate is provided on the side opposite to the model with guidance pads for secure repositioning into the compound structure.

33. An articulator apparatus according to claim 9, further comprising an iron plate disposed in the split cast plate having a magnetic acceptance and a brought-in magnet surrounded via a glue joint by an iron ring, the iron plate and magnetic acceptance forming a loosenable magnet system, them magnetic acceptance having a respective face, whereby the iron ring includes a face adjacent to the iron plate, which corresponds to the respective face of the magnetic acceptance and assures a position definition of a magnet iron ring system including the brought-in magnet, the glue joint and the iron ring and enables the split cast plate to be removed from the magnetic acceptance such that an iron core having a holding grip on the side of the magnet iron ring system without affecting the iron causes an increased adhesive force.

34. An articulator apparatus according to claim 9, wherein the articulator further comprises:
articulator columns;
jaw hinge heads including a ball callotte connected to the articulator columns, the jaw hinge heads rotating about the hinge-axis; and
an auxiliary mechanism which includes a transverse connection with a set screw and mobile carriages said mobile carriages including negatively conically formed recesses, and mounted screw elements, which are exactly superimposed with each other and are constructed such that the ball callotte is set in the negatively conically formed recesses, which are longitudinally variable via an adjusting screw inserted in the negatively conically formed recesses, the adjusting screw including an outer side point, a thread and guidance parts and which indicate on the outer side point a turning center of the hinge axis.

35. An articulator apparatus according to claim 9, wherein the having one of raised and recessed retention spots and the articulator mounting plate having one of raised and recessed retention elements are completely over-lapping and that thereby the one of the raised and recessed retention elements correspond with the one of the raised and recessed retention spots of the split cast plate such that the split cast plate and the articulator mounting plate exactly fit with each other and thus make a mounting position reproducable at any time.

* * * * *

UNITED STATES PATENT AND TRADEMARK OFFICE
CERTIFICATE OF CORRECTION

PATENT NO. : 5,190,455

DATED : March 2, 1993

INVENTOR(S) : Hans Schreiber

It is certified that error appears in the above-identified patent and that said Letters Patent is hereby corrected as shown below:

Col. 1, line 12, change "or" to --of--; and line 26, change "entering" to --entered--.

Col. 2, line 38, change "the" (first occurrence) to --take--, change "bead" to --head--.

Col. 7, line 33, change "arconarticulators" to --arcon-articulators--; and line 57, change "are" to --arc--.

Col. 8, line 39, after "15" insert --.--.

Col. 9, line 44, change "re-lief" to --relief--; and line 47, change "plat" to --plate--.

Col. 10, line 26, delete "4".

Col. 11, line 35, change "bying" to --lying--; and line 63, change "2" to --26--.

Col. 13, line 39, after "screw" insert --,--; and line 49, after "plate," insert --having a countersunk iron plate;--.

Col. 14, line 9, after "slot" insert --,--;

line 11, after "plate" insert --,--;

line 48, after "mechanism" insert --,--;

line 52, after "relief" insert --,--; and line 57, change "insert" to --inset--.

UNITED STATES PATENT AND TRADEMARK OFFICE
CERTIFICATE OF CORRECTION

PATENT NO. : 5,190,455
DATED : March 2, 1993
INVENTOR(S) : Hans Schreiber

It is certified that error appears in the above-identified patent and that said Letters Patent is hereby corrected as shown below:

Col. 15, line 24, after "models" insert --,--; and
line 59, after "can" insert --be--.

Col. 16, line 13, after "plate" insert --from--;
line 23, change "them" to --the--;
line 32, after "iron" insert --ring--; and
line 54, after "the" insert --split cast plate--.

Signed and Sealed this

Seventeenth Day of May, 1994

Attest:

BRUCE LEHMAN

*Attesting Officer*  *Commissioner of Patents and Trademarks*